United States Patent
McGinley (10) Patent No.: US 9,226,954 B2
(45) Date of Patent: Jan. 5, 2016

(54) METHOD FOR TREATING AND CONFIRMING DIAGNOSIS OF EXERTIONAL COMPARTMENT SYNDROME

(71) Applicant: Joseph McGinley, Casper, WY (US)

(72) Inventor: Joseph McGinley, Casper, WY (US)

(73) Assignee: Joseph C. McGinley, Casper, WY (US)

( * ) Notice: Subject to any disclaimer, the term of this patent is extended or adjusted under 35 U.S.C. 154(b) by 0 days.

(21) Appl. No.: 13/975,129

(22) Filed: Aug. 23, 2013

(65) Prior Publication Data

US 2014/0093455 A1 Apr. 3, 2014

Related U.S. Application Data

(63) Continuation-in-part of application No. 13/430,553, filed on Mar. 26, 2012.

(60) Provisional application No. 61/509,919, filed on Jul. 20, 2011, provisional application No. 61/692,627, filed on Aug. 23, 2012.

(51) Int. Cl.
| | | |
|---|---|---|
| A61K 38/48 | (2006.01) | |
| A61K 49/00 | (2006.01) | |
| A61B 5/00 | (2006.01) | |
| A61B 6/00 | (2006.01) | |
| A61B 8/08 | (2006.01) | |

(52) U.S. Cl.
CPC ............ *A61K 38/4893* (2013.01); *A61B 5/4519* (2013.01); *A61B 5/4848* (2013.01); *A61K 49/00* (2013.01); *A61B 6/504* (2013.01); *A61B 8/085* (2013.01)

(58) Field of Classification Search
None
See application file for complete search history.

(56) References Cited

U.S. PATENT DOCUMENTS

| | | | |
|---|---|---|---|
| 3,629,581 | A | 12/1971 | Smith |
| 3,766,384 | A | 10/1973 | Anderson |
| 5,217,488 | A | 6/1993 | Wu |
| 5,991,651 | A | 11/1999 | LaBarbera |
| 6,000,399 | A | 12/1999 | Choy |
| 6,326,020 | B1 | 12/2001 | Kohane et al. |
| 6,577,887 | B2 | 6/2003 | Wolff et al. |
| 6,708,693 | B1 | 3/2004 | Choy et al. |
| 7,381,186 | B2 | 6/2008 | Ueno et al. |
| 8,539,621 | B2 | 9/2013 | West |
| 2002/0193683 | A1 | 12/2002 | Danielsson et al. |
| 2005/0113663 | A1 | 5/2005 | Tamez-Pena et al. |
| 2005/0165293 | A1 | 7/2005 | Carter et al. |
| 2006/0025686 | A1 | 2/2006 | Ueno et al. |
| 2006/0257503 | A1 | 11/2006 | Eversole |
| 2007/0238949 | A1 | 10/2007 | Wang et al. |
| 2007/0258992 | A1 | 11/2007 | Atassi |
| 2008/0031414 | A1 | 2/2008 | Coppens |
| 2008/0200802 | A1 | 8/2008 | Bhavaraju et al. |
| 2009/0318802 | A1 | 12/2009 | Boyden et al. |
| 2010/0041765 | A1 | 2/2010 | Campbell et al. |
| 2012/0046540 | A1 | 2/2012 | Branch et al. |
| 2013/0204119 | A1 | 8/2013 | Coelho Do Sameiro Espregue Mendes |

FOREIGN PATENT DOCUMENTS

| | | |
|---|---|---|
| WO | 0228425 | 4/2002 |
| WO | 2010082837 A1 | 7/2010 |

OTHER PUBLICATIONS

Robert Eberhardt et al. Chronic Venous Insufficiency Circulation. 2005;111:2398-2409.*
Frink et al., Compartment Syndrome of the Lower Leg and Foot, Clin Orthop Relat Res (2010) 468:940-950.*
Tipton, Obturator neuropathy, Curr Rev Musculoskelet Med (2008) 1:234-237.*
Tucker, Chronic exertional compartment syndrome of the leg, Curr Rev Musculoskelet Med (2010) 3:32-37.*
Henry Gray, Anatomy of the Human Body.; The Arteries of the Lower Extremity. Downloaded online on Mar. 5, 2015.*
Bong et al. Chronic Exertional Compartment Syndrome Diagnosis and Management, Bulletin • Hospital for Joint Diseases, vol. 62, Nos. 3 & 4; 2005 P:77-84.*
A. Schubert, Exertional Compartment Syndrome: Review of the Literature and Proposed Rehabilitation Guidelines Following Surgical Release, Int J Sports Physical Therapy. 2011; 126-141.
Noticification Concerning Transmittal of International Preliminary Report on Patentability (Chapter I of the Patent Cooperation Treaty).

(Continued)

Primary Examiner — Michael G Hartley
Assistant Examiner — Nabila Ebrahim
(74) Attorney, Agent, or Firm — Marsh Fischmann & Breyfogle LLP (57) ABSTRACT

Described is a new method of treating chronic compartment syndrome in a muscle of a mammal, particularly exertional compartment syndrome. The method includes introducing an effective amount of a nerve-blocking toxin, such as human botulinum toxin into the muscle. Further in addition to treating chronic or exertional compartment syndrome, a method is included and described in the disclosure of confirming diagnosis of exertional compartment syndrome in a muscle of a mammal. In the method, venous compression and/or expansion in a mammal in an area of a muscle having a symptom associated with exertional compartment syndrome is evaluated by comparing venous flow at rest and after stress on the muscle. An anaesthetic is used to block a nerve supplying motor function to the muscle causing compression of a blood vessel. The mammal is evaluated after the block of the nerve to determine if the symptom associated with exertional compartment syndrome is alleviated.

6 Claims, 9 Drawing Sheets

(4 of 9 Drawing Sheet(s) Filed in Color)

(56) References Cited

OTHER PUBLICATIONS

Litwiller, et al., "Chronic exertional compartment syndrome of the lower extremeties: improved screening using a novel dual birdcage coil and in-scanner execise protocol," Skeletal Radiol, 2007, 36:1067-1075 Jan. 1, 2007.

http://chrisevans3d.com/files/reference/thigh_leg_muscles.pdf May 17, 2008.

Isner-Horobeti, et al., "Intramuscular Pressure Before and After Botulinum Toxin in Chronic Exertional Compartment Syndrome of the Leg: A Preliminary Study," The American Journal of Sports Medicine, 2013, 41:2558 (http://ajs.sagepub.com/content/41/2558) Aug. 22, 2013.

Medhelp, Botox for Peripheral Neuropathy; http://www.medhelp.org/posts/neurology/Botox-for-peripheral-neuropathy/show/452571 Mar. 1, 2008.

Styf, et al., "Intramuscular Pressue and Muscle Blood Flow During Exercise in Chronic Compartment Syndrome," British Editorial Society of Bone and Joint Surgery, vol. 69 B. 2, Mar. 1987, p. 301-305 Mar. 1, 1987.

Fraipont, et al., Chronic Exertional Compartment Syndrome, J Am Acad Orthop Surg 2003; 11:268-276 Aug. 1, 2003.

UWHC, "Common Regional Nerve Blocks," Quick Guide developed by UWHC Acute Pain Service, Jan. 1, 2011.

Gajraj, "Botulinumm Toxin A. Injection of the Obturator Internus Muscle for Chronic Perineal Pain," The Journal of Pain, vol. 6, No. 5, May 2005, pp. 333-337 May 1, 2005.

Ferre, MD, et al., "Emergency physicians can easily obtain ultrasound images of anatomical landmarks relevant to lumbar puncture," American Journal of Emergency Medicine, 2007, 25, 291-296 Jan. 1, 2007.

Lecocq, et al., "Exercise-induced compartment syndrome treated by botulinum toxin," Abstract/Annals of Physical and Rehabilitation Medicine 54S, 2011 e124-e125 Jan. 1, 2011.

* cited by examiner

METHOD FOR TREATING AND CONFIRMING DIAGNOSIS OF EXERTIONAL COMPARTMENT SYNDROME

CROSS-REFERENCE TO RELATED APPLICATION

This application is a continuation-in-part of U.S. patent application Ser. No. 13/430,553 filed Mar. 26, 2012, entitled "METHOD FOR TREATING AND CONFIRMING DIAGNOSIS OF EXERTIONAL COMPARTMENT SYNDROME" which claims priority to U.S. Provisional Patent Application No. 61/509,919, filed Jul. 20, 2011, entitled "METHOD FOR TREATING AND CONFIRMING DIAGNOSIS OF EXERTIONAL COMPARTMENT SYNDROME" and also claims priority to U.S. Provisional Patent Application No. 61/692,627, filed Aug. 23, 2012, entitled "METHOD FOR TREATING AND CONFIRMING DIAGNOSIS OF VASCULAR OBSTRUCTION SECONDARY TO VASCULAR COMPRESSION" the entire disclosure of which is incorporated herein by reference.

BACKGROUND OF THE INVENTION

1. Field of the Invention

The invention relates to the field of treatment of a mammal having exertional compartment syndrome and methods for confirming diagnosis of compartment syndrome resulting from vessel compression, overuse or other vascular stress, and more particularly to a method of non-surgically treating and confirming diagnosis of humans, including athletes, having exertional compartment syndrome.

2. Description of Related Art

Chronic exertional compartment syndrome, also known as exercise-induced compartment syndrome, is a disease that generally impacts athletes and can be debilitating. It is caused by reversible ischemia in an affected compartment. Various etiologies have been proposed, but the actual cause is believed not to have yet been proven. Typical treatment is fascial release of the affected compartment.

In the disease, the patient may feel pain, for example, in the calf which increasingly worsens with exercise. Exertional compartment syndrome is severely painful and more often than not affects high level athletes. The pain typically centers in the calf muscles and progressively worsens with higher levels of activity. The pain is sometimes described by patients as increasing pain and pressure under the skin. The symptoms can seem to the patient to get progressively worse but, in the case of advanced athletes, they may continue to train and exercise to meet goals.

It is believed that the symptoms of pain and tightness are the result of pressure that builds up within a muscle(s) of a patient, typically in a limb such as the leg or arm and most typically in the leg. As muscles are surrounded by tight tissue known as fascia, in normal use, the fascia has sufficient space for allowing muscles to function properly. However, in the case of athletes or other exertional use, as activity increases, so does blood flow to the muscle. Muscle size increases, but if the fascia is too constrictive, blood flow to the constricted muscle can be interrupted. Lack of blood flow leads to ischemia and associated pain.

Currently there are non-surgical steps to alleviate symptoms but no non-surgical treatments. Physicians may prescribe rest, physical therapy, or changes in exercise habits to alleviate symptoms, but these recommendations do not always work and do not treat the underlying disease.

If non-surgical recommendations for alleviating symptoms are ineffective, typical treatment is a surgery on the affected muscle compartment or compartments, which are generally in the leg. The surgery itself is not always successful with some patients having recurrent symptoms months to years later. Such surgery is the primary treatment of chronic exertional compartment syndrome, and currently the most effective. In the surgery, the physician operates on the fascia, the inelastic tissue encasing muscle compartments. A fasciotomy involves cutting open the fascia of each affected compartment. Alternatively, a surgery may include actually removing a portion of the fascia, known as a fasciectomy. The surgery is intended to release or decompress the area so the compartment can release pressure otherwise blocked by the fascia.

Complications of such surgeries include infections, nerve damage (which can be permanent) caused by inadvertent cutting or damage to nerves while undertaking the surgery, scarring and numbness in the area. There are also cosmetic issues in that muscles may appear to enlarge during exercise due to the lack of normal fascia containment.

Other non-surgical symptom treatments and/or preventative paths have also been suggested, including transdermal vitamin D3 treatment as described in International Patent Publication WO 2010/082837 A1 and use of preventative supplements to avoid the disease as described in U.S. Patent Publication No. 2006/0257503A1. The latter publication suggests a supplement for avoiding occurrence of compartment syndrome caused by a variety of pathways including exertional compartment syndrome in the forearm associated with "muscle pump" in professional motocross athletes. The publication describes a nutritional ingestible supplement mixture including magnesium chelate, malic acid, diethylglycine HCl and niacinamide which is intended to reduce the occurrence of the disease.

Much work has been done to improve diagnosis of the disease pathway (see, e.g. U.S. Pat. No. 7,381,186 directed to measuring pressure build-up in muscles). However, needs in the art still exist to confirm diagnosis and properly identify the etiology of the disease and also to provide better, more reliable, less invasive and preferably non-surgical treatment for compartment syndrome due to vessel compression, overuse, stress and the like, particularly exertional compartment syndrome.

BRIEF SUMMARY OF THE INVENTION

The invention herein includes a method of treating exertional compartment syndrome in a muscle of a mammal. The method comprises introducing an effective amount of a nerve-blocking toxin into the muscle. The muscle is preferably located in a limb of the mammal, such as a leg. The muscle is preferably at least one of the adductor longus muscle, the sartorius muscle, the vastus intermedius muscle, the adductor magnus muscle, the popliteus muscle, the gastrocnemius muscle, the soleus muscle, and/or the plantaris muscle, and the mammal is preferably a human.

In an embodiment herein, the nerve blocking toxin is a human botulinum toxin, and more preferably the toxin is onabotulinumtoxin A, otherwise commercially known and available as BOTOX®. Preferably, the human botulinum toxin is in solution form and diluted, for example, with saline or a similar suitable delivery solution.

The method may further comprise introducing human botulinum toxin adjacent a blood vessel in an area of the muscle wherein there is a blood vessel compression and/or expansion. In one embodiment herein, the mammal is a human, the muscle is the adductor longus muscle, the sartorius muscle, the vastus intermedius muscle and/or the adductor magnus muscle, the area is adjacent a blood vessel in an area of the muscle experiencing symptoms. In a further embodiment, the mammal is a human, the human botulinum toxin is introduced in a proximal area of the muscle to be treated adjacent to a blood vessel. The method may also further comprise introducing the human botulinum toxin into the muscle percutaneously through at least one injection.

In the method, preferably, an effective amount of human botulinum toxin to be used is about 50 units to about 600 units, more preferably about 50 to about 300 units, most preferably about 50 to about 150 units, and in one embodiment, about 100 units.

The method in an embodiment herein may further comprise introducing the human botulism percutaneously through at least one injection into an area of the muscle adjacent a blood vessel under compression and/or expansion, wherein the muscle is at least one muscle elected from an adductor muscle, a sartorius muscle, a vastus intermedius muscle, an adductor magnus muscle, a popliteus muscle, a gastrocnemius muscle, a soleus muscle and/or a plantaris muscle. In such embodiment, the method preferably further comprises introducing the human botulinum toxin into first and second areas of the muscle, each adjacent a blood vessel under compression and/or expansion percutaneously through a first percutaneous injection, wherein a distal end of a needle is located in a first area, and a second percutaneous injection, wherein a distal end of a second needle is located in the second area, for example, by injecting human botulinum toxin in two injections, into areas of each leg of a patient to be treated. The effective amount in such embodiment may be about 50 units to about 300 units. More preferably about half of the effective amount is introduced through each of the first needle and the second needle.

If desired, the method can also comprise anaesthetizing the skin or a percutaneous area of the mammal prior to the at least one injection in an area of an injection site.

The method may also comprise identifying vascular anatomy through use of ultrasound prior to the at least one injection, and confirming placement of a distal end of a needle(s) within the muscle for use in the at least one injection via use of computer tomography (CT), magnetic resonance imaging (MRI) and/or sonographic technology.

The invention also includes a method of treating exertional compartment syndrome in a muscle of a human, comprising introducing about 50 units to about 600 units of a human botulinum toxin into an area of the muscle adjacent a blood vessel under compression and/or expansion.

In yet another embodiment, a method of treating exertional compartment syndrome in at least one of an adductor longus muscle, a sartorius muscle, a vastus intermedius muscle, an adductor magnus muscle, a popliteus muscle, a gastrocnemius muscle, a soleus muscle and/or a plantaris muscle of a human is provided. The method comprises introducing about 50 units to about 300 units of a human botulinum toxin into an area of the muscle adjacent a blood vessel under compression and/or expansion.

The invention also incorporates a method of confirming diagnosis of exertional compartment syndrome in a muscle of a mammal, comprising evaluating venous compression and/or expansion in a mammal in an area of a muscle having a symptom associated with exertional compartment syndrome by comparing venous flow at rest and after stress on the muscle; using an anaesthetic to block a nerve or a branch thereof supplying motor function to the muscle causing the symptom; and evaluating the mammal after the block of the nerve or the branch thereof to determine if the symptom associated with exertional compartment syndrome is alleviated.

In the method of confirming diagnosis of exertional compartment syndrome in a muscle of a mammal noted above, the venous compression and/or expansion may be evaluated through CT angiography, ultrasound, magnetic resonance (MR) angiography, angiography and/or MRI in the area of the muscle.

In an embodiment of the method of confirming diagnosis of exertional compartment syndrome in a muscle of a mammal, the mammal is preferably a human, the muscle is one or more of the adductor longus muscle, the sartorius muscle, the vastus intermedius muscle and/or the adductor magnus muscle. The blocked nerve may be an obturator nerve or a branch thereof. Preferably the blocked nerve is an anterior branch of the obturator nerve. In addition, preferably venous compression and/or expansion are evaluated on a femoral vein and a calf vein(s). In a further embodiment, the muscle is a popliteus muscle, a gastrocnemius muscle, a soleus muscle and/or a plantaris muscle. The blocked nerve may be one or more of an obturator nerve, a perineal nerve, a tibial nerve, a sciatic nerve and/or branches thereof.

BRIEF DESCRIPTION OF THE SEVERAL VIEWS OF THE DRAWING(S)

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. The patent or application file contains at least one drawing executed in color. Copies of this patent or patent application publication with color drawings will be provided by the Office upon request and payment of the necessary fee.

In the drawings.

DETAILED DESCRIPTION OF THE INVENTION

The invention provides innovations in the art concerning diagnosis and treatment of exertional compartment syndrome. The diagnostic method herein confirms such diagnoses usually made by physicians by confirming that venous compression and/or expansion in an area of the muscle affected by symptoms is the etiology of the disease, by demonstrating also that such symptoms can be alleviated by blocking nerve action in the area. Based on such diagnostic research, the applicant herein also discovered a new non-surgical treatment of exertional compartment syndrome using a nerve-blocking toxin such as human botulinum toxin. Such venous compression and/or expansion can occur anywhere along the deep venous system in the leg, in either the calf or thigh, leading to exertional compartment syndrome.

As used herein, "compartment" refers to muscles and associated nerves and vessels located within a generally non-compliant collagenous membrane otherwise known as a fascia. "Exertional Compartment syndrome" refers to a disease associated with increased pressure within a compartment through swelling and/or bleeding or other conditions within the compartment that compress or otherwise affect blood vessel flow within the compartment causing pain and/or other symptoms in a mammal or any other compartment syndrome caused by stress, overuse or other associated cause of vascular compression. Typically such exertional compartment syndrome is caused by extended exercise, sports, or other source of muscular stress as can be caused by physical exertion that can lead to chronic compartment syndrome, also known as exertional compartment syndrome or exercise-induced compartment syndrome.

For the purpose of illustrating the invention, information and description herein are provided with a focus on exertional compartment syndrome, although it should be understood by one skilled in the art based on this disclosure that various forms of compartment syndrome involving vascular compression from a variety of causes may be diagnostically confirmed and/or treated by the methods provided herein.

As used herein, "mammal" refers to a human or animal having muscular tissue and associated vasculature and nervous system and that may develop chronic or acute pain as a result of exertional compartment syndrome. Although animals having such characteristics are also within the scope of the invention, for the purposes of best illustrating the methods herein, the detailed description is based on treatment of a human patient, but one skilled in the art would understand that similar principles and diagnostic and treatment methods could be applied to animals provided the effective amount were directed to an animal and not a human.

As used herein, a "limb" is an arm or leg. For the purpose of illustrating the invention, the detailed description herein refers to a leg and, more specifically to a muscle in the leg in the thigh or calf. Details are provided herein with the example of the adductor longus muscle; as such muscle can be associated with exertional compartment syndrome. However, the invention should not be seen as restricted thereto, and can be applied to treatment of various forms of chronic compartment syndrome, including exertional compartment syndrome, for example, in the arm or other body locations. In the leg, the treatment may be administered in one or more of the adductor longus, sartorius, vastus intermedius muscles, adductor magnus muscle, popliteus muscle, gastrocnemius muscle, soleus muscle, and the plantaris muscle, with the adductor longus being a common area for treatment.

Various compartments within the leg can also be treated depending on where venous compression and/or expansion is experienced, for example, treatment may occur in the anterior compartment, the deep posterior compartment, the superficial posterior compartment and/or the lateral compartment, wherein, for example, various venous compression and/or expansion may be experienced on the anterior tibial vein in the anterior and lateral compartments, on the posterior tibial vein and/or perineal vein in the deep posterior compartment, and in the popliteal vein and/or gastrocnemius vein in the superficial compartment. Blockage sites thus can occur in the popliteal and femoral veins of the thigh as well as in the locations noted above in the calf area of the leg.

The method includes the step of introducing an effective amount of a nerve blocking toxin such as human botulinum toxin into the muscle. The human botulinum toxin preferred is as onabotulinumtoxin A, which is commercially available and FDA approved, and also known in the art as BOTOX®. BOTOX® is known as a sterile, lyophilized form of botulinum toxin type A, which is produced from a culture of the Hall strain of *C botulinum*. It is purified by various acid precipitations into a crystalline complex having the toxin and other proteins. It is distributed in 100-unit vials.

Other nerve blocking toxins, such as other forms of human botulinum toxin may also be used, including DYSPORT which is sold, for example, in Europe, is made using column-based purification methods and is sold in 500-unit vials. Dysport is also a botulinum toxin type A preparation, but differs from BOTOX® in its potency which is about four times greater than BOTOX® on a per unit basis, however, a Dysport dose can be about four times a BOTOX® dose to generate a similar clinical effect. The differences are generally associated with differences in strain, method of making, diffusion, and potency testing.

Thus, other forms of nerve blocking toxins, such as human botulinum toxin may be used, but the effective amount needed for treatment will have to be adjusted from those recommended herein which are base on the preferred embodiment of BOTOX®.

Preferably, as administered, a human botulinum toxin is introduced in solution form and diluted with a delivery fluid, such as saline. However, other solutions, wherein the human botulinum toxin is not diluted or wherein it is diluted with other known solutions which may be used and/or introduced into a muscular area are within the scope of the invention. Also within the scope of the invention is the ability to combine the human botulinum toxin in solution with other medicaments for treatment of the area of the muscle to which the human botulinum toxin is to be introduced. For example, it is possible to introduce steroids and similar anti-inflammatory treatments, when a patient experiences muscle pain. In preparing the human botulinum toxin, typically, the commercially available dosage is reconstituted with saline, and depending on the desired dosage, can vary in terms of the amount of saline to be used. Dilutions are indicated based on the desired injection and dosage size. The higher the dose in one injection, and less dilute the injection need be, and the more dilute the solution, the lesser the dosage amount in a given injection. Thus, different dilutions may apply if one is introducing the dosage for a given leg in more than one injection.

The preferred human botulinum toxin is preferably in liquid form as noted above, and is preferably introduced into the effected muscle tissue. The preferred location for introduction of the nerve-blocking toxin is the proximal area of the affected muscle preferably adjacent a blood vessel running through the muscle which blood vessel (veins and/or arteries) extends generally longitudinally and in an area where such blood vessel(s) are under compression and/or expansion. As shown, a blood vessel runs generally longitudinally and through a canal. However, it should be understood that such generally longitudinally extending vessels need not be in a canal and can run through an area of the muscle in a generally longitudinal direction from a proximal end of the muscle. Typically, a muscle where a patient is experiencing exertional compartment syndrome has blood vessels in the form of veins and arteries, and branches of such veins and arteries. The area also has nerves extending within the muscle that function to provide motor function to the muscle.

It should be understood by one skilled in the art, based on this disclosure, that while the proximal area of the affected muscle is exemplified herein for treatment to minimize the blocking effect, the injection can be made more distally or proximally if it is desired by the physician and/or patient for some reason to block the area further. For example, a dosage may be introduced either in the case that the initial injection was not sufficient or if the patient requires more blocking treatment and does not need a lot of lateral movement (e.g., for a runner who needs long muscle and not a lot of lateral movement like a soccer player). Thus, the location should not otherwise be considered limiting to the scope of the invention herein and treatments can be varied according to desired outcome in terms of range of movement and blocking effect.

Figure 1A:
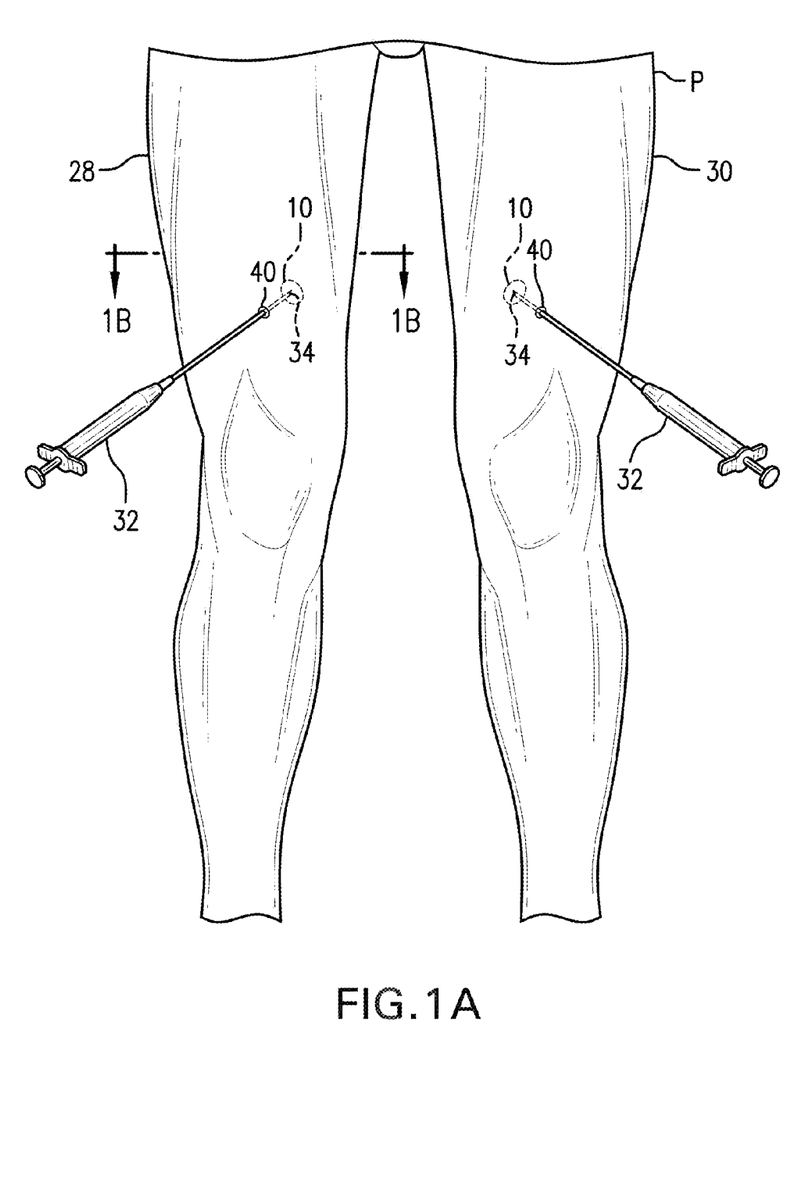
FIG. 1A is a view of a patient having an injection site for a treatment according to an embodiment of a treatment method herein.
Figure 1B:
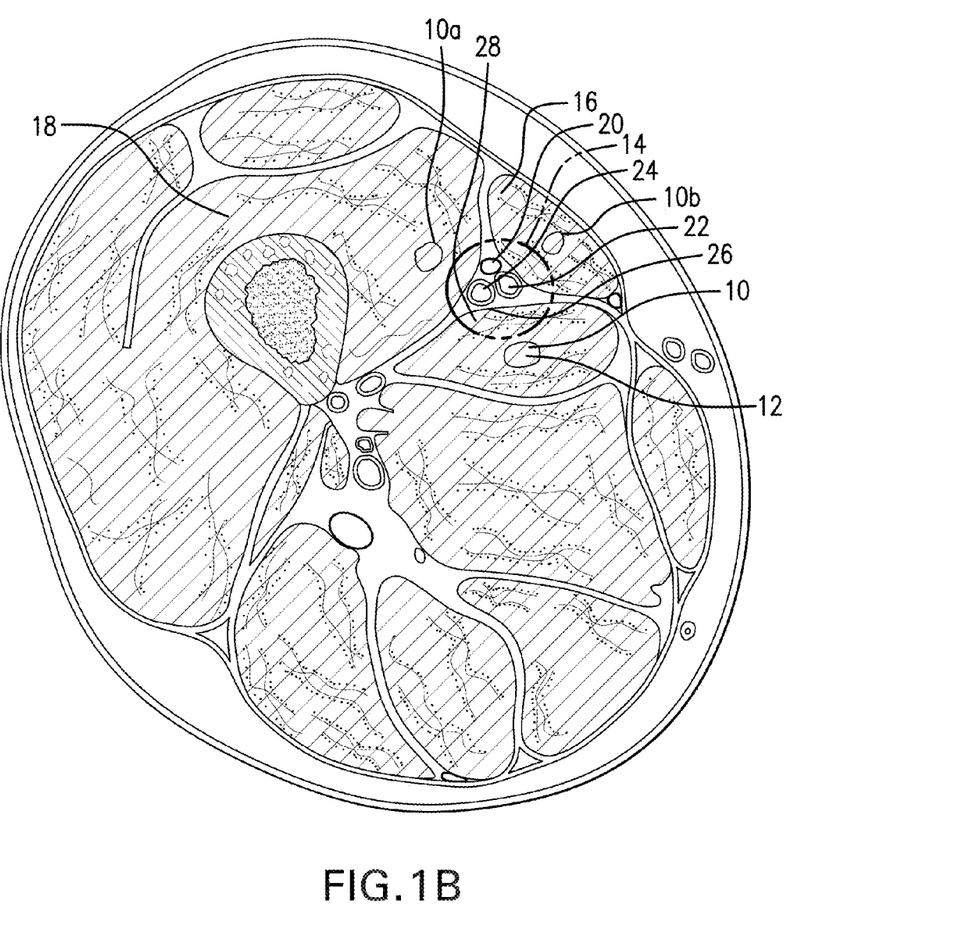
FIG. 1B is an enlarged transverse cross-sectional representation of the leg of a patient of FIG. 1A showing an adductor longus muscle and adductor canal taken along line 1B-1B.
Figure 6:
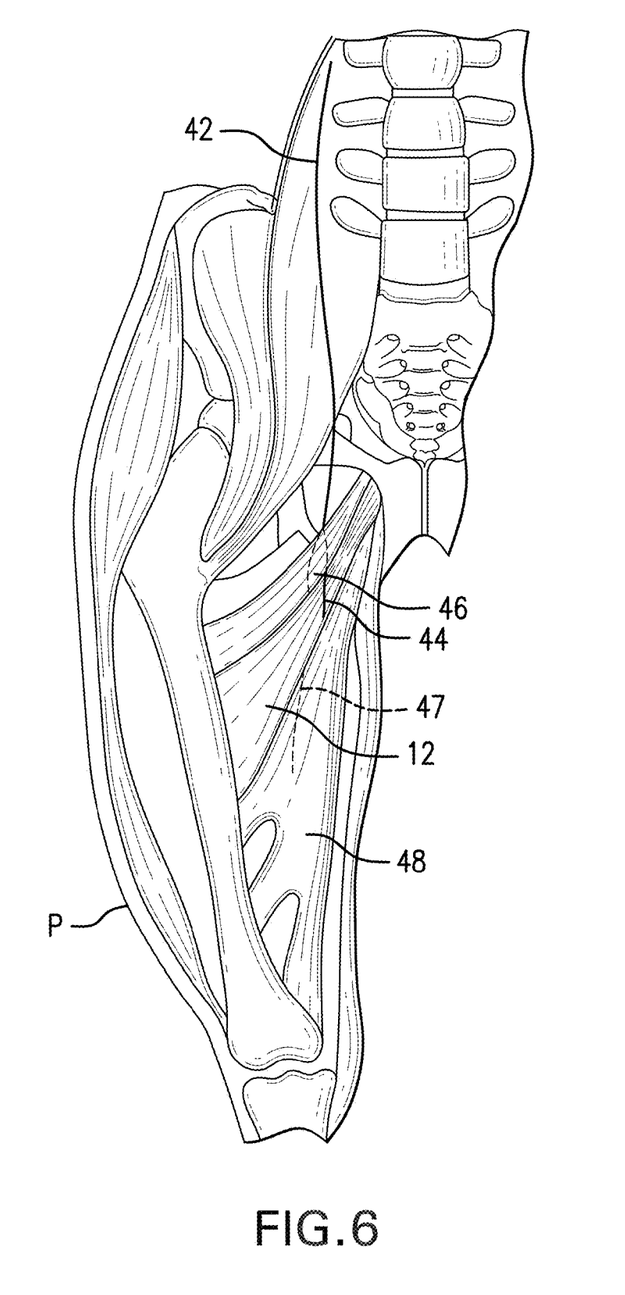
FIG. 6 is a graphic illustration showing location of the obturator nerve and adductor longus muscle.

A specific treatment will now be illustrated as an example with reference to the adductor longus muscle as shown in FIG. 1B and FIG. 6. However, similar treatments of the other various muscles which may be causing symptoms by compression and/or expansion of a blood vessel as noted above would occur in a similar and analogous manner and so this example is provided for illustration of treatment of all such muscles. The distal area 10 through which the nerve-blocking toxin is to be introduced for the adductor longus muscle 12 is shown in FIG. 1B and FIG. 6. A canal, here, the adductor canal 14 is shown in a representation of a cross-sectional view of the muscle. The canal 14 is located among the sartorius muscle 16, the vastus intermedius muscle 18 and the adductor longus muscle 12. The canal 14 has running therethrough the saphenous nerve 20 and the femoral vein 22 and femoral artery 24. The human botulinum toxin is introduced into area 10 into the adductor longus muscle 12 near to the border 26 of the adductor canal 14 so as to be adjacent the compressed and/or expanded blood vessel. The precise location can vary depending on the patient's anatomy and the desired effects. As used herein being "adjacent" to the blood vessel means that the injection occurs in an area wherein an effective amount of human botulinum toxin will operate to have an effect on symptoms of exertional compartment syndrome. In preferred examples herein, "adjacent" thus also includes about 5 to about 10 mm from the blood vessel, although this will vary depending on patient, location and dose of the toxin.

Techniques for introducing nerve-blocking toxin such as human botulinum toxin into the area of the muscle affected for treatment may vary, including embolization using delivery microspheres of varying polymeric materials known in the art or to be developed, biodegradeable and non-biodegradable drug delivery microspheres or implantable devices, catheters and other transmission lumens, and injectible solutions. As an example, in one embodiment herein, the human botulinum toxin is introduced into an area such as area 10 of the muscle, such as adductor longus muscle 12 percutaneously through at least one injection using a needle having a lumen extending therethrough and a container at the proximal end of the needle for introducing the human botulinum toxin in liquid form, such as diluted with saline, for example, into the lumen of the needle. The container may be a standard syringe body or separate coupleable container having a preloaded dosage therein. Preferably a needle is used having a gauge of about 18 to about 40 gauge, more preferably about 20 to about 30 gauge, and most preferably about 20 to about 25 gauge is used. Suitable needles include needles generally used for anesthesia and other procedures, including spinal needles.

In a preferred embodiment, and with reference to FIGS. 1A, 1B and 6, human botulinum toxin is introduced through two such injectible needle devices 32 into the same area 10 posterior to the adductor canal 14 in each patient leg. For example, in facing a patient, an injection may be made on a left side 28 of the patient in the left leg and one may be made on the right side 30 of the patient in the right leg. Each injection is outside the border 26 of the adductor canal 14 and in the distal area 10 of the adductor longus muscle 12. In using two injections, and two needles 32, the amount administered would preferably be divided generally equally between the needles. The invention is not restricted however, to needle injection, or if using needle injection, using two such needles, with one in each leg. In fact, one needle can be used for one or more injections in a serial manner, two or more needles can be used to administer the human botulinum toxin serially or simultaneously.

Further, the dosage may be broken up into different needle injections in each of the patient's legs, provided the recommended total dosage is not exceeded. Multiple injections, each having a portion of the total recommended dosage for one side of the body in one leg may also be made near the canal in the area 10 or in other areas in adjacent muscles on opposite or other sides of the canal 14. According to one embodiment herein, the adductor longus is being treated and is small and easy to access, however, injections may be introduced in similar locations 10a, 10b in other muscles such as in the sartorius muscle 18 or vastus intermedius muscle(s) 16, respectively or in any other leg muscles in similar locations, including within the adductor magnus, the popliteus muscle, the gastrocnemius muscle, the soleus muscle, and/or the plantaris muscle. Thus, one can introduce several injections in only one muscle, inject a portion of a dosage in each of two or three muscles, etc., and the amount injected in two or more muscles in one leg need to be even.

When the dosage or portion thereof is injected into the muscle(s), it is preferred that it is injected away from the motor end plate of the muscle, i.e., where the nerves communicate, generally located in the proximal third of the muscle. It is preferred that the dosage is administered to only block distally, i.e., furthest inwards towards the far end of the canal. One may also inject at, for example, the medial head or the lateral head of the gastrocnemius muscle.

As one moves closer to center of body, it is possible to block the entire muscle. To be conservative in treatment, it is preferred to inject in a proximal end of the muscle and adjacent a vessel under compression and/or expansion from the surrounding muscle. Thus, the number of injections and the ability to treat one or both legs using such injections (or other introductory methods) should be understood to be subject to variation based on this disclosure provided that the treating physician not administer more than the recommended dosage in total.

As noted above, and with reference to FIG. 1A, the nerve-blocking toxin is preferably injected percutaneously into an area of the adductor longus muscle adjacent the affected blood vessel through a first percutaneous injection wherein a distal end 34 of a needle 32 is located on a first side 28 of a patient in a first area 10 of a patient's left leg and a second percutaneous injection wherein a distal end 36 of a second needle 38 is located on a second side 30 of a patient in a second area 10 in the patient's other leg. The location will of course vary with the location of the muscle to be injected within the leg.

The amount administered will vary depending on the type of toxin, such as human botulinum toxin to be administered, however, with respect to the preferred use of onabotulinumtoxin A, in the form of commercially available BOTOX®, the effective amount preferably about 50 units to about 600 units, more preferably about 50 to about 300 units, and most preferably about 50 to about 150 units, and most preferred about 100 units. With respect to BOTOX®, the units used for dosing are expressed in mouse units, wherein one such unit is equal to the amount that kills 50% of a group of 18- to 22-g Swiss Webster mice when injected intraperitoneally. The human lethal dose (LD) for botulinum type A purified neurotoxin complex is currently listed as approximately 3000 units. BOTOX® injections are approved, for example, for cosmetic use at less than about 100 units and about 300-600 units for other non-cosmetic purposes aside from the invention herein for safety reasons. Dosing would of course vary for different forms of human botulinum toxin. Thus, the proposed effective amounts of BOTOX® for the novel treatment herein is within what are believed in the medical arts to be safe use limits for patients.

In the treatment method herein, it is also preferred due to the nature of the use of an injectible solution and a somewhat larger gauge needle to anaesthetize the skin and injection site area, for example as shown in FIG. 1A a first injection site 40 on the patient P prior to administering the at least one injection in the area of an injection site to alleviate discomfort. Suitable numbing techniques, for example, lidocaine and the like may be used as are known in the art or to be developed.

To ensure accurate injection it is also preferred to determine the proper area for placement of the distal end(s) of the needles prior to insertion. One technique for doing this is to first properly identify and review the vascular anatomy in the area through use of ultrasound, X-ray, endoscopy, CT angiography, MRI, MR angiography, angiography or similar instrumentation or techniques known or to be developed in the art for visualizing the internal area prior to proceeding. Preferably ultrasound is used to identify the anatomy and then also sonography, CT and/or MRI is used to confirm proper placement of a distal end(s) of needle(s) within the muscle area. Such techniques are known in the art and the invention is not intended to be limited by any particular technique for visualizing the vascular anatomy or ensuring proper placement of the needle ends prior to introducing the human botulinum toxin.

As noted above, before engaging in the treatment method, the etiology of the exertional compartment syndrome disease being treated can be confirmed. Diagnoses for such syndrome are typically made by introducing needles into compartments and measuring the pressure. The patient then exercises on a tread mill and the compartment pressure is measured again. Such measurements can be made, for example, using equipment as described in U.S. Pat. No. 7,381,186, incorporated herein in relevant part by reference.

If a diagnosis is made that a patient has chronic compartment syndrome, such as exertional compartment syndrome, the diagnosis can be confirmed by first evaluating the patient using instrumentation to evaluate the venous flow in the effected muscle so diagnosed at rest and after stress on the muscle. Preferred ways of doing this include use of CT angiography, ultrasound, MR angiography, angiography and/or MRI to evaluate venous anatomy and behavior, including venous compression and/or expansion in a mammal, such as a human patient in the area of a muscle having symptoms associated with compartment syndrome (such as chronic or acute pain, particularly chronic and severe pain when exercising or stressing a muscle). The instrumentation or other technique, such as the use of CT angiography, ultrasound, MR angiography, angiography and/or MRI can be used, for example, to compare venous flow when the patient is at rest and after stress on the muscle. Thus, the physician has confirmation that there is a definable distinction that is not normal reaction of a healthy unaffected muscle.

Following this evaluation, the physician preferably blocks a nerve or nerve branch responsible for supplying motor function to the muscle causing the symptom in the area affected. If one is blocking an entire nerve, it is preferred, for example to use a block such as lidocaine on the nerve end. Bupivicaine may also be used. Any suitable nerve blocking technique may be used, as is known in the anaesthetic and/or medical treatment arts, however, it is preferred that the nerve be blocked by techniques guided by sonography in a manner known in the art or to be developed. Examples of this procedure are known in the art. See for example, T. Saranteas et al., *Identification Of The Obturator Nerve Divisions And Subdivisions In The Inguinal Region: A Study With Ultrasound*, Acta Anaesthiol. Scand. 2007; 51:1404-1406; Y. Fujiwara et al., *Obturator Nerve Block Using Ultrasound Guidance*, Anesth. Analg. 2007; 105:888-889; P. E. Helayel et al., *Ultrasound-Guided Obturator Nerve Block: A Preliminary Report Of A Case Series*, Reg. Anest. Pain Med. 2007; 32:221-226; and J. Soong, et al., *Sonographic Imaging Of The Obturator Nerve For Regional Block*, Reg Aesth Pain Med. 2007; 32:146-151, the relevant portions of which are incorporated herein by reference.

After the nerve block is in effect, the patient is then preferably evaluated again to determine if the symptom(s) previously observed and believed associated with the chronic compartment syndrome is/are alleviated. If so, the diagnosis is now confirmed and the disease etiology clearly identified.

As an example in one embodiment herein, in a case of exertional compartment syndrome in the area of an adductor longus muscle, such technique can be applied by first evaluating the venous behavior in the area of the adductor longus muscle effected using CT angiography (or other instrumentation) on both legs in that area at rest and after stress on the muscle. Venous compression and/or expansion are preferably thus evaluated on a femoral vein and a calf vein(s) for comparative purposes. A block is then applied to the obturator nerve or a branch thereof. As shown in FIG. 6 which is representative and partial illustration of the relevant internal anatomy of an upper portion of a leg of a patient P, the obturator nerve 42 is located on a side of the adductor longus muscle 12. Preferably, the block is applied to an anterior branch 44 of the obturator nerve 42. The obturator nerve 42 descends towards the pelvis and after passing through the obturator foramen, the obturator nerve enters the medial aspect of the thigh, and divides into the anterior branch 44, which is located between the adductor longus muscle 12 and the brevis muscle 46. The posterior branch 47 of the obturator nerve lies between the adductor brevis muscle 46 and adductor magnus muscle 48.

Various nerves and branches thereof can be blocked for use in the diagnostic method herein without departing from the scope of the invention.

The method may be used on patients while still in a cast, and in many cases, treatment can be applied, for example, in the medial and/or lateral head of the gastrocnemius muscle in the calf, even with the cast still applied. Treatments may be applied successfully within the proximal third of the muscle in the upper portion thereof, adjacent a blood vessel, such as a vein, in an area of compression. The CT scan findings enable location of the area affected, for example of vessel compression rendering the treatment an easily injectible procedure in the affected area to alleviate symptoms.

The invention will now be described with respect to the following non-limiting examples of the methods for diagnosis and treatment as described above herein:

EXAMPLE

A young female athlete was evaluated herein who had been clinically diagnosed as having exertional compartment syndrome of the calf. The patient was a 16 year old, competitive cross-country skier, runner and soccer player with symptoms of progressive debilitating pain in the calf with intense excise. Compartment measures demonstrated significant elevation of pressure in the deep and superficial posterior compartments of the calf at 1 min. and 5 min. post-exercise.

Figure 2A:
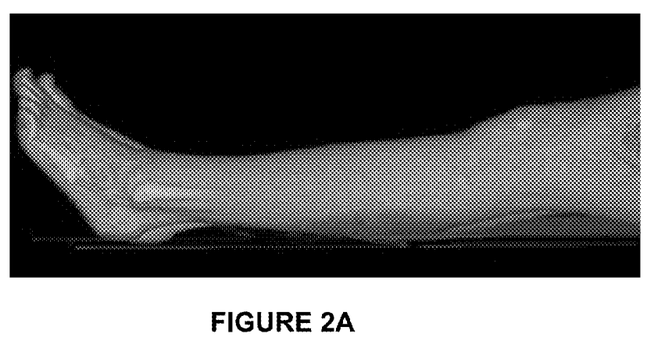
FIG. 2A is a volume rendered CT image with the legs of the patient in the Example at rest.
Figure 2B:
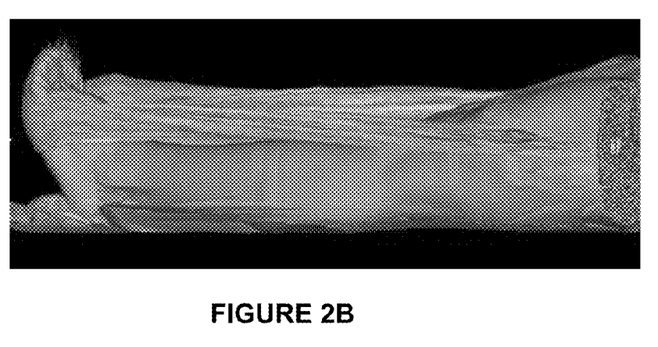
FIG. 2B is a volume rendered CT image with the legs of the patient in the Example stressed by plantar flexing the feet against resistance provided by a sheet wrapped around the feet.
Figure 3A:
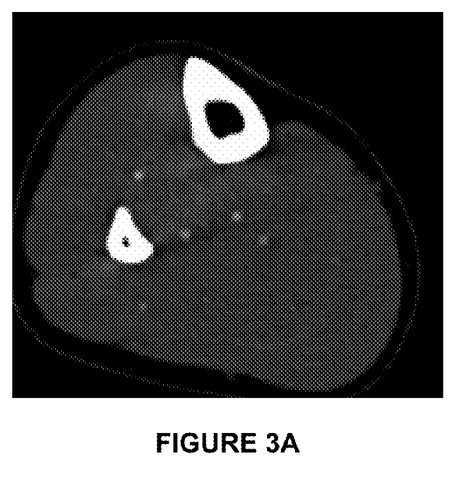
FIG. 3A is an axial contrast enhanced CT image of the patient in the Example at rest demonstrating normal vascular performance within the posterior calf muscles.
Figure 3B:
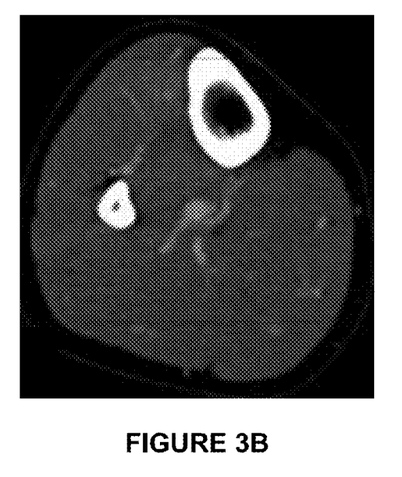
FIG. 3B is a further, repeat image after stress maneuvers demonstrating extensive abnormal venous engorgement in the posterior calf muscles.

The patient underwent a CT angiogram (volume rendered computer tomography images and axial contrast enhanced computer tomography images were taken) of the bilateral legs which demonstrated normal venous flow at rest (see CT images in FIGS. 2A and 3A). With provocative maneuvers, the patient had engorgement of the calf vein and also compression of the femoral vein in the adductor canal (see CT images in FIGS. 2B and 3B).

Figure 4:
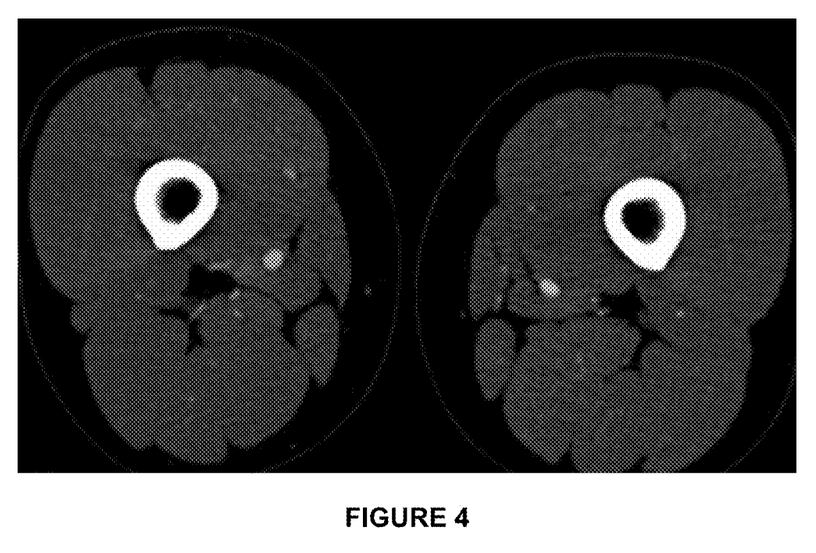
FIG. 4 is an axial CT image at the level of the distal adductor canal of the patient in the Example demonstrating arterial opacification with complete compression of the femoral vein during stress maneuvers.
Figure 5A:
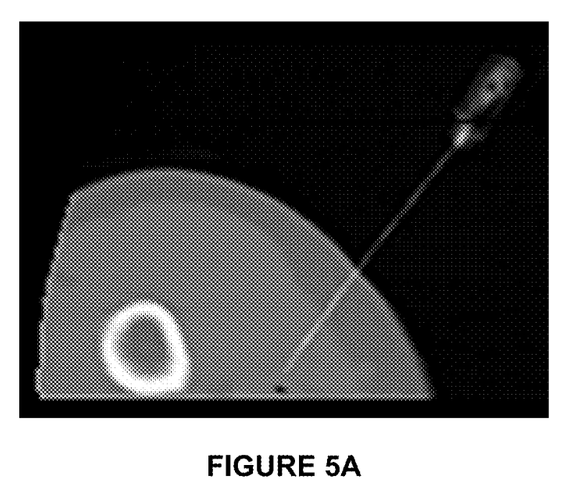
FIG. 5A is an axial CT image demonstrating needle placement in the distal adductor longus muscle for injection of BOTOX.
Figure 5B:
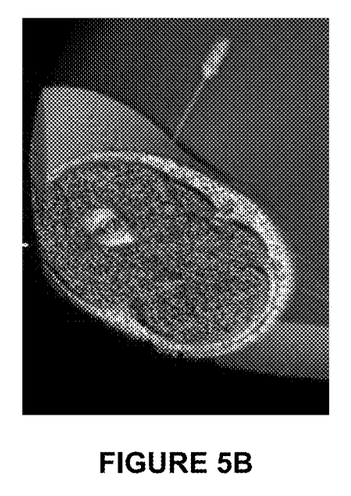
FIG. 5B is a volume rendered CT image demonstrating needle placement in the adductor longus muscle for injection of BOTOX.

As shown in FIG. 4, the axial image of the CT scan at the level of the distal adductor canal demonstrates arterial opacification with complete compression of the femoral vein during stress maneuvers. Images suggested compression by the muscles surrounding the adductor canal with a large contribution from the adductor longus muscle. To test the theory of venous compression by the adductor longus muscle, the anterior branch of the obturator nerve was blocked using sonographic guidance (FIGS. 5A and 5B) in both legs and a repeat CT angiogram performed with stress maneuvers. Thus, a nerve block was undertaken using ultrasound guidance and administration of lidocaine and bupivicaine. The area was first localized with lidocaine and bupivicaine, the skin anaesthetized, and a 25 gauge needle introduced lidocaine and bupivicaine into the muscle in the area to be blocked.

Figure 7:
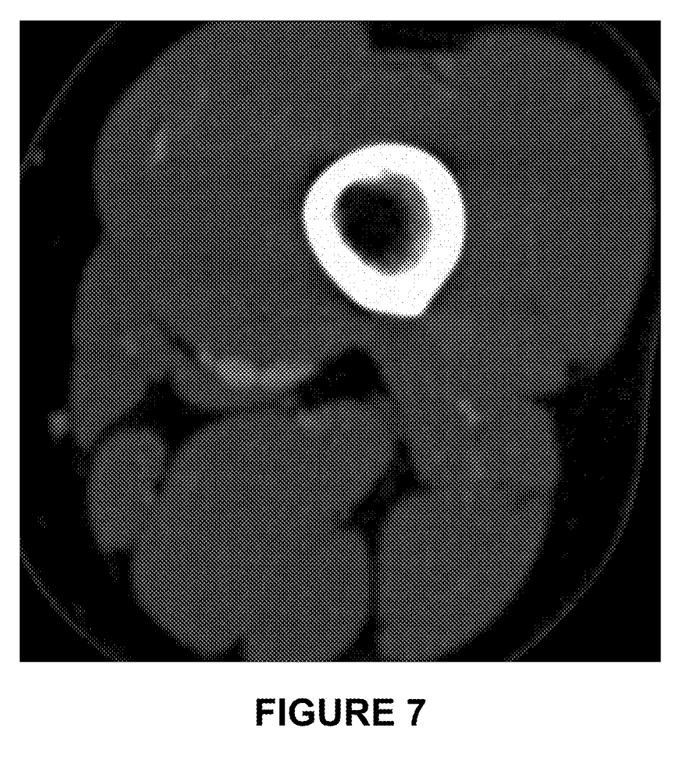
FIG. 7 is a CT scan image of the adductor canal of the patient in the Example after obturator nerve block with stress maneuvers, showing only minimal compression of the femoral nerve.

Following the nerve block, the CT angiogram showed decreased engorgement of the calf veins with approximately 50% reduction in the degree of femoral vein narrowing in the adductor canal. See, FIG. 7. Furthermore the patient was completely asymptomatic while maintaining stress maneuvers for over 60 s (symptoms were present at 10 s pre-blockage).

A targeted botulinum toxin injection was then undertaken of the distal aspect of the adductor longus at the posterior border of the adductor canal. Using sonographic and CT guidance, the distal end of 25-gauge needles were placed in the muscle belly of the adductor longus in each leg at its distal portion. Following this, 50 units of onabotulinumtoxin A (BOTOX®) were injected into a site in an area near and posterior to the adductor canal outside its border under sonographic visualization.

Figure 8A:
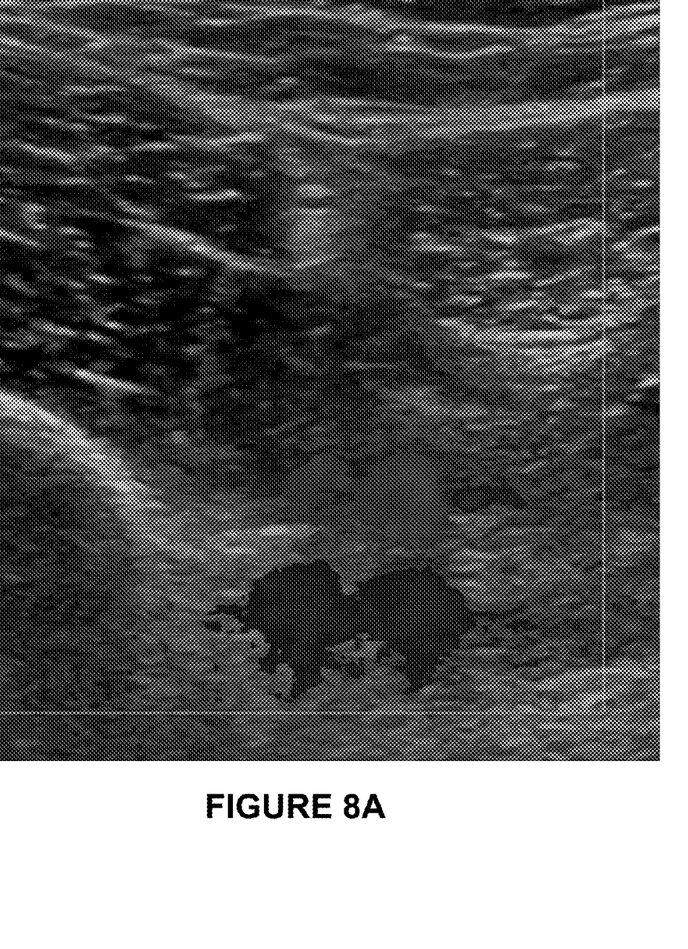
FIGS. 8A and 8B are ultrasound images of the adductor canal of the patient in the Example three weeks after treatment with human botulinum toxin demonstrating that the femoral artery (shown in red) and femoral vein (shown in blue) both at rest and under stress, respectively, show no compression.
Figure 8B:
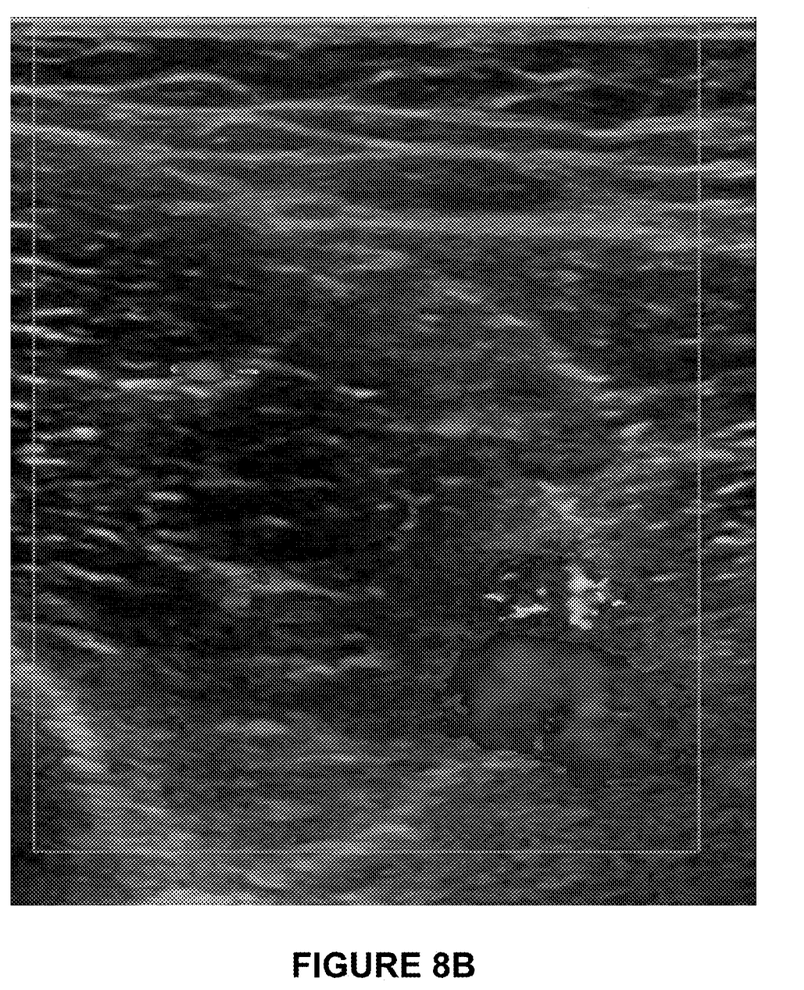

The patient gradually returned to activity, achieving full activity at three weeks. The patient returned for a follow-up ultrasound with and without stress maneuvers at three weeks post injection. Scans were taken at rest and under stress. There was no evidence of venous compression under stress maneuvers on sonographic imaging. See, FIGS. 8A and 8B. Furthermore the patient was completely asymptomatic at full activity and no adverse side effects were observed or reported. The patient noticed minimal weakness with lateral motion at full activity; however this improved with continued training. The patient achieved five weeks post treatment being completely asymptomatic while competing at full activity. The patient stated at the time that her legs had not felt as good in over a year.

The patient continues to be observed. The example supports a new diagnosis confirmation method and a non-surgical treatment method for exertional compartment syndrome, with complete resolution of symptoms and no adverse affect on athletic performance.

Procedure: A preliminary ultrasound of the bilateral adductor canal was performed identifying the vascular anatomy with both gray-scale and color Doppler images as well as the adductor longus muscle. The overlying soft tissues were subsequently prepped and draped in typical sterile fashion. A 1% lidocaine solution was used to anaesthetize the skin and overlying soft tissue at the level of the adductor canal bilaterally. Subsequently, a 25-gauge spinal needle was advanced under sonographic guidance into the distal aspect of the adductor longus muscle. The right side was performed first followed by the left side with representative images acquired and stored. After initial placement of the needle, a limited CT scan was performed demonstrating positioning of the needle tip for each needle. The needles were slightly adjusted under sonographic guidance and a repeat CT scan was performed. Once there was confirmation of needle tip placement within the distal adductor longus muscle, approximately 50 units of human botulinum toxin were injected into each adductor longus muscle. Each leg had 50 units diluted into 2 cc of normal saline. The injection was performed under sonographic guidance with subsequent CT imaging demonstrating the injection fluid within the distal third of the adductor longus muscle. No evidence of post procedural complications. The patient was monitored for approximately 15-30 minutes following the procedure with no adverse reactions. A follow-up phone call to the patient was placed the day following the injection and again, the patient was asymptomatic from the injection with just some minor bruising and pain at the injection site.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of confirming diagnosis of exertional compartment syndrome a mammal, comprising:

identifying a first muscle in the mammal having a symptom associated with exertional compartment syndrome;

evaluating venous compression of a vein by a second muscle by comparing venous flow in the vein at rest and after stress on the first and second muscles, wherein the second muscle is at a location in the mammal downstream of the first muscle relative to a venous return flow in the vein and the first and second muscles are different;

injecting an anaesthetic at the second muscle to block a nerve or a branch of the nerve supplying motor function to the second muscle to immobilize at least a portion of the second muscle compressing the vein; and evaluating the symptom in the first muscle after the block of the nerve or the branch of the nerve supplying motor function to the second muscle to determine if the symptom associated with compartment syndrome is alleviated.

2. The method according to claim 1, wherein the venous compression is evaluated through computerized tomography angiography, ultrasound, magnetic resonance angiography, angiography and/or magnetic resonance imaging of at least the second muscle.

3. The method according to claim 1, wherein the mammal is a human and the second muscle is at least one of an adductor longus muscle, a sartorius muscle, a vastus intermedius muscle, or an adductor magnus muscle.

4. The method according to claim 3, wherein the blocked nerve is an anterior branch of the obturator nerve.

5. The method according to claim 3, wherein the venous compression is evaluated on a femoral vein in the adductor canal.

6. The method according to claim 1, wherein the mammal is a human and the first muscle is at least one of a popliteus muscle, a gastrocnemius muscle, a soleus muscle, or a plantaris muscle.

* * * * *